United States Patent
Khurd et al.

(10) Patent No.: US 9,047,660 B2
(45) Date of Patent: Jun. 2, 2015

(54) NETWORK CYCLE FEATURES IN RELATIVE NEIGHBORHOOD GRAPHS

(71) Applicants: Parmeshwar Khurd, Princeton, NJ (US); Ali Kamen, Skillman, NJ (US); Hari Sundar, Austin, TX (US); John V. Frangioni, Wayland, MA (US); Summer Gibbs-Strauss, Cambridge, MA (US)

(72) Inventors: Parmeshwar Khurd, Princeton, NJ (US); Ali Kamen, Skillman, NJ (US); Hari Sundar, Austin, TX (US); John V. Frangioni, Wayland, MA (US); Summer Gibbs-Strauss, Cambridge, MA (US)

(73) Assignees: Siemens Corporation, Iselin, NJ (US); Beth Israel Deaconess Medical Center, Boston, MA (US)

( * ) Notice: Subject to any disclaimer, the term of this patent is extended or adjusted under 35 U.S.C. 154(b) by 98 days.

(21) Appl. No.: 13/780,370

(22) Filed: Feb. 28, 2013

(65) Prior Publication Data

US 2013/0243292 A1    Sep. 19, 2013

Related U.S. Application Data

(60) Provisional application No. 61/605,578, filed on Mar. 1, 2012.

(51) Int. Cl.
*G06T 7/00* (2006.01)
*G06K 9/46* (2006.01)
*G06K 9/62* (2006.01)
*G06T 17/00* (2006.01)

(Continued)

(52) U.S. Cl.
CPC .............. *G06T 7/0012* (2013.01); *A61B 6/5229* (2013.01); *G06T 17/20* (2013.01); *G06T 7/0032* (2013.01); *G06T 2207/10056* (2013.01); *G06T 2207/20072* (2013.01); *G06T 2207/30024* (2013.01)

(58) Field of Classification Search
CPC ....... G06K 9/46; G06K 9/469; G06K 9/6211; G06T 17/00; G06T 17/005; G06T 17/20; G06T 7/0012; G06T 7/001; G06T 7/40; G06T 2207/10072; G06T 2207/10081; G06T 2207/10096; G06T 2207/10104; G06T 2207/10108; G06T 2207/10116; G06T 2207/30081; G06T 2207/30096; A61B 6/032; A61B 6/52; A61B 6/5211; A61B 6/5294
USPC .......... 382/128, 131, 132, 133, 181, 204, 224
See application file for complete search history.

(56) References Cited

U.S. PATENT DOCUMENTS 7,706,633 B2    4/2010  Chefd'hotel et al.
7,899,764 B2 *  3/2011  Martin et al. ................... 706/12

(Continued)

OTHER PUBLICATIONS

Doyle, et al. "Automated Grading of Prostate Cancer using Architectural and Textural Image Features." Biomedical Imaging: From Nano to Macro. (2007): 1284-1287. Print.*

(Continued)

*Primary Examiner* — Michael A Newman

(57) ABSTRACT

Methods for analyzing biomedical data include: (a) obtaining macroscopic imaging data; (b) obtaining histopathological imaging data; (c) executing a parallel algorithm stored on a non-transient computer-readable medium to compute one or a plurality of network cycle features of a relative neighborhood graph derived from the histopathological imaging data; (d) registering the macroscopic imaging data and the histopathological imaging data; and (e) correlating the macroscopic imaging data and the network cycle features. Systems for analyzing biomedical data and computer readable storage media are described.

20 Claims, 10 Drawing Sheets

(51) Int. Cl.
  *A61B 6/03* (2006.01)
  *A61B 6/00* (2006.01)
  *G06T 17/20* (2006.01)

(56) References Cited

U.S. PATENT DOCUMENTS

| | | | | |
|---|---|---|---|---|
| 8,130,221 | B2* | 3/2012 | Voth | 345/420 |
| 8,812,431 | B2* | 8/2014 | Voigt et al. | 706/54 |
| 2005/0260583 | A1* | 11/2005 | Jackway et al. | 435/6 |
| 2010/0111396 | A1* | 5/2010 | Boucheron | 382/133 |
| 2010/0290685 | A1 | 11/2010 | Wein et al. | |
| 2011/0026794 | A1 | 2/2011 | Sundar et al. | |
| 2011/0040169 | A1* | 2/2011 | Kamen et al. | 600/411 |
| 2011/0122226 | A1 | 5/2011 | Kamen et al. | |
| 2011/0216954 | A1 | 9/2011 | Sundar et al. | |
| 2012/0106821 | A1* | 5/2012 | Madabhushi et al. | 382/133 |
| 2014/0064580 | A1* | 3/2014 | Madabhushi et al. | 382/128 |

OTHER PUBLICATIONS

Cignoni, et al. "Parallel 3D Delaunay Triangulation." Eurographics. 12.3 (1993): C-129-C-142. Print.*
Tsymbal, et al. "Neighborhood Graph and Learning Discriminative Distance Functions for Clinical Decision Support." 31st Annual International Conference of the IEEE EMBS. (2009): 5617-5620. Print.*
Bilgin, et al. "Cell-Graph Mining for Breast Tissue Modeling and Classification." Proceedings of the 29th Annual International Conference of the IEEE EMBS. (2007): 5311-5314. Print.*
Boucheron, et al. "Histopathological Image Analysis: A Review." IEEE Rev Biomed Eng. 2. (2009): 147-171. Print.*
Boucheron, Laura. Object- and Spatial-Level Quantitative Analysis of Multispectral Histopathology Images for Detection and Characterization of Cancer. Diss. University of California, 2008. Print.*
Fernandez-Gonzalez, et al. "A Tool for the Quantitative Spatial Analysis of Complex Cellular Systems." IEEE Transactions on Image Processing. 14.9 (2005): 1300-1313. Print.*
Connor, et al. "Fast construction of k-Nearest Neighbor Graphs for Point Clouds." IEEE Transactions on Visualization and Computer Graphics. (2009): 1-11. Print.*
Doyle et al. "Automated Grading of Prostate Cancer using Architectural and Textural Image Features." Biomedical Imaging: From Nano to Macro. (2007): 1284-1287. Print.*
Hendrickson, et al. "Graph Analysis with High-Performance Computing." Computing in Science & Engineering. (2008): 14-19. Print.*
Cignoni et al. "Parallel 3D Delaunay Triangulation." Eurographics. 12.3 (1993): C-129-C-142. Print.*
Andrade, et al. "Good Approximations for the Relative Neighbourhood Graph." Proceedings of the 13th Canadian Conference on Computational Geometry (CCCG'01) (2001): 25-28. Print.*
M. Gurcan et al., "Histopathological Image Analysis: A Review," IEEE Reviews in Biomedical Engineering, vol. 2, pp. 147-171, 2009.
C. Gunduz et al., "The cell graphs of cancer," Bioinformatics, vol. 20(1), pp. i145-i151, 2004.
P. Khurd et al., "Network Cycle Features: Application to Computer-Aided Gleason Grading of Prostate Cancer Histopathological Images," In: Int. Symp. Biomedical Imaging, IEEE, pp. 1632-1636, 2011.
T. Franiel et al., "Prostate MR Imaging: Tissue Characterization with Pharmacokinetic Volume and Blood Flow Parameters and Correlation with Histologic Parameters," Radiology, vol. 252(1), pp. 101-108, 2009.
J. P. Monaco et al., "High-throughput detection of prostate cancer in histological sections using probabilistic pairwise Markov models," Medical Image Analysis, vol. 14, pp. 617-629, 2010.
R. Urquhart, "Algorithms for computation of relative neighbourhood graph," Electronics Letters, vol. 16(14), pp. 556-557, 1980.
H. Sundar et al., "Bottom-Up Construction and 2:1 Balance Refinement of Linear Octrees in Parallel," Abstract, SIAM Journal of Scientific Computing, vol. 30(5), pp. 2675-2708, 2008.
A. N. Chernikov et al., "Algorithm 872: Parallel 2D Constrained Delaunay Mesh Generation," ACM Transactions on Mathematical Software (TOMS), vol. 34(1), pp. 6:1-6:20, 2008.
M. Chen, "A parallel 3D Delaunay triangulation method," Ninth IEEE International Symposium on Parallel and Distributed Processing with Applications, pp. 52-56, 2011.
G. E. Blelloch et al., "Design and Implementation of a Practical Parallel Delaunay Algorithm," Algorithmica, vol. 24(3), pp. 243-269, 1999.
P. Cignoni et al., Parallel 3D Delaunay Triangulation, Abstract, pp. 1-12, (1993).
A. Chekkoury et al., "Automated Malignancy Detection in Breast Histopathological Images," In Proc. SPIE Medical Imaging, SPIE, 2012, pp. 1-13.
B. Milic et al., "Dropped Edges and Faces' Size in Gabriel and Relative Neighborhood Graphs," In IEEE International Conference on Mobile Adhoc and Sensor Systems (MASS), pp. 407-416, 2006.
F. Zhang et al., "Face Tracing Based Geographic Routing in Nonplanar Wireless Networks," In INFOCOM, pp. 2243-2251, IEEE, 2007.
H. Sundar et al., "Parallel Algorithms for the Computation of Cycles in Relative Neighborhood Graphs," Abstract, pp. 1-9, (2012).

* cited by examiner (a) MORTON PARTITIONING     (b) IMAGE PARTITIONING

NETWORK CYCLE FEATURES IN RELATIVE NEIGHBORHOOD GRAPHS

RELATED APPLICATIONS

This application claims the benefit of U.S. Provisional Application No. 61/605,578, filed Mar. 1, 2012, the entire contents of which are incorporated herein by reference, except that in the event of any inconsistent disclosure or definition from the present specification, the disclosure or definition herein shall be deemed to prevail.

FEDERALLY SPONSORED RESEARCH AND DEVELOPMENT

This invention was made with government support under Contract No: CA134493 awarded by National Institutes of Health (NIH). The government has certain rights in the invention.

TECHNICAL FIELD

The present teachings relate generally to parallel computation of network cycle features in relative neighborhood graphs and, more specifically, to the application of these network cycle features in a variety of domains including but not limited to the biomedical field.

BACKGROUND

Relative neighborhood graphs (RNGs) and their variants, such as Gabriel graphs, have been proposed as methods for connecting a set of points by edges so that the resulting graph characterizes the perceived shape of the point-set. Both RNGs and Gabriel graphs are special cases of general shape-encoding graph constructs called β-skeletons. Relative neighborhood graphs can play an important role in a variety of applications, such as morphological processing in computer vision, pattern classification problems, geographical analysis, and wireless networking.

In spite of the utility of RNGs and the potential for their application in a variety of important fields, computation of cycle lengths and perimeters of RNGs becomes extremely difficult as the size of the problem increases (e.g., whole-mount histopathology slides, large-scale wireless networks spanning a continent, star systems, etc.). In the case of histopathological image analysis, there are significant computational challenges involved in studying correlations between macroscopic imaging biomarkers—for example, MR data—and histopathological network cycle features—for example, a prostatectomy whole-mount slide—because the computations involve several thousand MR voxels and several million nuclei. Moreover, an MR voxel maps onto an irregular region in histopathological slides due to various deformations (e.g., expansion after prostatectomy, tissue cuts and tears during microtome use, tissue dehydration during staining, etc.) involved in the process, such that computation of the average network cycle lengths over an irregular region becomes necessary.

SUMMARY

The scope of the present invention is defined solely by the appended claims, and is not affected to any degree by the statements within this summary.

By way of introduction, the presently preferred embodiments described herein include methods, systems, instructions, and computer-readable storage media for biomedical analysis. The presently preferred embodiments provide for parallel computation of network cycle features of RNGs. In histopathological applications, this parallel computation facilitates correlation between macroscopic imaging biomarkers of a disease and graph-theoretic microscopic biomarkers of the RNGs derived from histopathological imaging data.

A first method for analyzing biomedical data embodying features of the present teachings includes: (a) obtaining macroscopic imaging data; (b) obtaining histopathological imaging data; (c) executing a parallel algorithm stored on a non-transient computer-readable medium to compute one or a plurality of network cycle features of a relative neighborhood graph derived from the histopathological imaging data; (d) registering the macroscopic imaging data and the histopathological imaging data; and (e) correlating the macroscopic imaging data and the network cycle features.

A second method for analyzing biomedical data embodying features of the present teachings includes: (a) obtaining histopathological imaging data; (b) executing a parallel algorithm stored on a non-transient computer-readable medium to compute one or a plurality of network cycle features of a relative neighborhood graph derived from the histopathological imaging data; and (c) predicting a presence and/or severity of a disease using the network cycle features, and/or correlating graph-theoretic microscopic biomarkers with the presence and/or severity of the disease.

A system for analyzing biomedical data embodying features of the present teachings includes: (a) a memory operable to store macroscopic imaging data and histopathological imaging data; (b) a processor operable to (I) generate a relative neighborhood graph from the histopathological imaging data by parallel computation; (ii) compute one or a plurality of network cycle features of the relative neighborhood graph by parallel computation; and (iii) correlate the macroscopic imaging data and the network cycle features; and (c) a display operable to display an analysis result derived from correlation of the macroscopic imaging data and the network cycle features.

A computer readable storage medium embodying features of the present teachings has stored therein data representing instructions executable by a programmed processor for biomedical study, the storage medium including instructions for: (a) generating a relative neighborhood graph from histopathological imaging data by parallel computation; (b) computing one or a plurality of network cycle features of the relative neighborhood graph by parallel computation; and (c) correlating the macroscopic imaging data and the network cycle features.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Parallel algorithms for computing cycle orders and cycle perimeters in relative neighborhood graphs (e.g., Urquhart approximations) have been discovered and are described hereinbelow. These parallel algorithms have wide-ranging applications from microscopic (e.g., histopathological image analysis) to macroscopic (e.g., wireless network routing) to astronomic (e.g., identify candidates for black holes within a star system) domains. In some embodiments, the relative neighborhood graphs are derived from histopathological image data, and the parallel algorithms enable the study of correlations between macroscopic imaging biomarkers (e.g., of a cancer, including but not limited to prostate cancer) and graph-theoretic microscopic biomarkers. Moreover, in some embodiments, the parallel algorithms can enable rapid automated Gleason scoring or cancer detection in cancer biopsy slides.

As further described below, a representative algorithm embodying features of the present teachings includes: (1) uniform partitioning of graph vertices (e.g., nuclei) across processes; (2) parallel Delaunay triangulation; and (3) parallel computation of a relative neighborhood graph and its cycle orders and perimeters. Algorithms in accordance with the present teachings were evaluated and excellent fixed-size (strong) and isogranular (weak) scalability were demonstrated.

Figure 1:
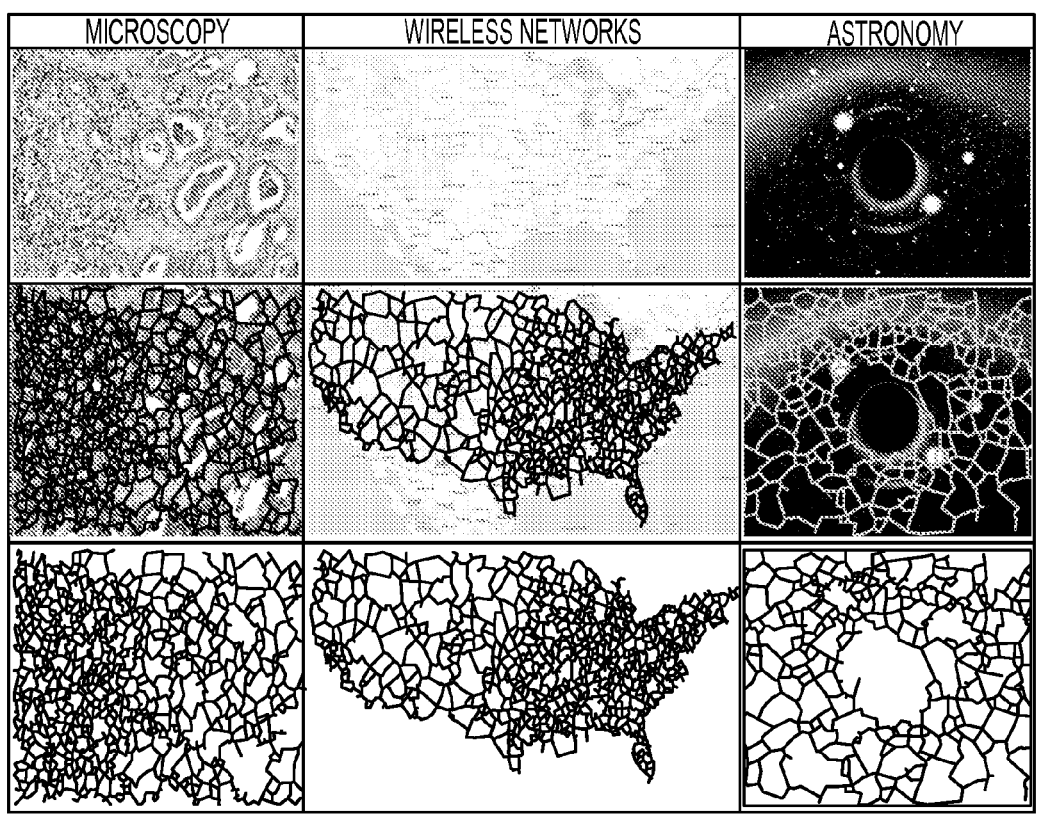
FIG. 1 shows example RNGs characterized by extremely large cycles in the fields of microscopy (left column), wireless networks (middle column), and astronomy (right column).

By way of general introduction, cycle tracing in a graph provides an important characterization of the topological properties of the graph. It has found applications in a wide variety of fields ranging from wireless routing to malignancy detection and grading in histopathological images. Applications of the cyclical characteristics of RNGs in microscopic, macroscopic, and even astronomic domains are envisioned. By way of example, FIG. 1 shows three large cycles for RNGs in three different applications. In each of (a), (b), and (c), the top row shows the original image, the second row shows the image overlaid with the RNG, and the last row shows the RNG by itself. As further described below, identifying large cycles in Urquhart graphs can enable the identification of items of interest including but not limited to (a) irregular cell arrangements characteristic of cancer, (b) areas with low cellular coverage, and (c) black holes.

In FIG. 1(a), the vertices correspond to cell nuclei and the large cycles in the bottom row correspond to irregular glands or tubular structures. While neither desiring to be bound by any particular theory nor intending to limit in any measure the scope of the appended claims or their equivalents, it is presently believed that high average cycle perimeters are a sign of malignancy. In FIG. 1(b), the vertices correspond to locations in a sensor or wireless network, and the large cycles in the bottom row correspond to regions with inadequate coverage. Finally, in FIG. 1(c), the vertices correspond to astronomical bodies (e.g., stars), and the large cycles in the bottom row correspond to star-free regions, which may be of interest for further astronomical study (e.g., as candidates for the existence of black holes). As presently contemplated, the algorithms, methods, and systems described herein can be used in studying data from any of these representative applications as well as others. With regard to applications in astronomy, the use of three-dimensional version of RNGs and a corresponding three-dimensional face-tracing algorithm may be more appropriate in some embodiments. Although low local vertex density estimates obtained via Parzen windowing can also indicate large cycles, explicit cycle tracing provides more information about the topology and requires no interpolation operations.

The RNG is an undirected graph defined on a set of points, V, in the Euclidean plane by connecting two points p and q with an edge whenever there does not exist a third point r closer to both p and q than they are to each other. The RNG is a subgraph of the Delaunay triangulation and the Euclidean minimum spanning tree is a subgraph of the RNG, which establishes lower and upper bounds for the number of edges in the RNG(V). For a set of n vertices, V, the number of edges in RNG(V) can be expressed as shown in Equation (1):

$$n-1 \le |RNG(V)|_e \le 3n-6. \quad (1)$$

For the case of RNGs computed from random point configurations characterized by a spatially homogeneous Poisson point process, an exact expression is available for the average number of edges dropped from the Delaunay network in order to obtain the RNG. Assuming a homogeneous density $\lambda > 0$ for the Poisson point process, its definition implies that the number of points in region S has a Poisson distribution with mean $\lambda A_S$, where $A_S$ is the area of region S. Let lune(p, q) denote the region containing points that are at a smaller distance to vertex p or vertex q than r=d(p,q), the distance between p and q. Its area is $$A_{lune(p,q)} = \left(\frac{2\pi}{3} - \frac{\sqrt{3}}{2}\right)r^2.$$

For a fixed vertex p, by multiplying the probabilities that a vertex q lies in an infinitesimal annulus at a distance r away from p and the probability that a third point exists in lune(p,q), the expression shown in Equation (2) is provided for the probability η that an edge pq in a disk of radius R centered at p gets dropped from the Delaunay network while obtaining the RNG:

$$\eta = \frac{\int_0^R \left(1 - e^{-\lambda A_{lune}(p,q)}\right) 2\lambda \pi r \, dr}{\lambda \pi R^2} \quad (2)$$

Using the expression of Equation (2), the average number of edges in the Delaunay triangulation, and Euler's formula for connected graphs, a formula for the average cycle order in the Poisson RNG can also be obtained. The expression in Equation (2) is extensible to the case of a spatially inhomogeneous Poisson process using a space-variant density $\lambda(x,y)$ using the same chain of reasoning. However, as presently understood, there is no known expression for average cycle perimeter even in the special case of a homogeneous Poisson process.

The Urquhart graph is a good approximation of the RNG that is obtained by removing the longest edge from every triangle in the Delaunay triangulation. An even simpler approximation to the RNG (viz., the removal of long edges above a threshold) may be used. All of these graphs are examples of pruned Delaunay networks obtained by removing a specific set of edges from the Delaunay triangulation. Other graphs may be used.

Heretofore, Urquhart's method has not been parallelized. While a linear-time (in the number of edges) sequential algorithm for cycle (face) computation in general planar graphs exists, this face-tracing algorithm uses the Heffter-Edmonds rotation system. This face-tracing algorithm can be parallelized using a modification of the algorithm described herein. However, the algorithm described herein is considerably faster because only the edges that are removed from the Delaunay network are processed and the overhead of setting up a rotation system is unnecessary.

As this stage, various parallel algorithms for computing average cycle lengths given an input image or a point cloud will be described. If the input is an image, feature detection methods are first used to extract feature coordinates from the images. This extraction is application specific, and some standard approaches are briefly discussed below. Once the features (coordinates) are obtained, these points are first uniformly distributed across all processes to ensure load-balance for the subsequent stages. This is followed by computing the Delaunay triangulation of these points in parallel, followed by the parallel computation of the RNG (e.g., Urquhart's approximation of the RNG) and thereby the cycles.

The high-level pseudocode for the overall algorithm is presented in Algorithm 1 shown below. For all algorithms described herein, the components requiring inter-process communication are identified with a par prefix. The remaining components do not involve any communication or synchronization and standard sequential codes can be used without any modification. As further explained below, a key challenge in parallelization of the RNG construction and cycle computation is that cycles can span across processor boundaries and a naïve parallelization requires parallel searches leading to heavy synchronization costs if done iteratively. By performing upfront communication of inter-process boundaries using non-blocking point-to-point communication, expensive synchronization costs can be avoided and excellent strong and weak scalability obtained.

---
Algorithm 1 Parallel Computation of Cycle Lengths
---

1: x ← Features
2: par_Partition x, p

---
Algorithm 1 Parallel Computation of Cycle Lengths
---

Figure 3:
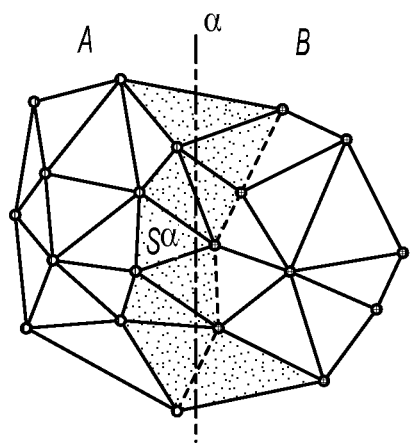
FIG. 3 shows an example RNG having an overlap region between processes.

3: $\Gamma_x$ ← ConvexHull x
4: S ← par_Delaunay x, $\Gamma_x$, p
5: par_Cycles S, p In the description below, the following notation is to be understood: N refers to the global number of points, which are divided amongst p processors or processing instances, and n refers to the number of points on a given processor. Assuming optimal partitioning, N=np. A graph G=(E, V) is defined in terms of the vertices, V and the edges E. The number of edges and the number of vertices in a graph are given by $|\mathcal{G}|_e$ and $|\mathcal{G}|_v$ respectively. $e_{ij}$ refers to the edge shared between polygons i,j and its length is given by $|e_{ij}|$. The order (number of sides) of a polygon i is given by $\mathcal{O}$ i and its perimeter by Ci. The point-set is denoted by the vector x, its convex hull by $\Gamma_x$, and its Delaunay network by S. With a slight abuse of notation, the same symbols are used to denote both the overall point-set as well as the process-specific point-set depending upon the context. As shown in FIG. 3, the subset of Delaunay triangles intersecting an inter-process boundary line α is denoted by $S^\alpha$. Points are partitioned between processors A(red) and B(blue) using quadtree partitioning. An overlap is needed to generate triangulations connecting these boundaries. Both processors will independently generate the triangles in the overlap region, $S^\alpha$, before starting on their own local points. The shortest inter-process boundary minimizing the number of longest edges is shown in orange, and defines the ownership of the triangles. In the representative example shown in FIG. 3, all except one triangle from $S^\alpha$ belong to process A.

For embodiments in which the input is an image, feature detection methods can be used to extract features points from image patches. Any supervised or unsupervised methods for feature point detection may be used, addressing the specific problems encountered during two-dimensional imaging of three-dimensional features. Special-purpose methods for specific structures, such as cell nuclei, may be used. In some embodiments, depending upon the feature detection performance requirements, simple operations such as thresholding and non-maximum suppression might suffice (such as in FIG. 1(c)), whereas in other embodiments, more complex operations might be necessary. In general, feature detection methods are embarrassingly parallel and can be load balanced based on the image size. By way of example, a linear SVM is trained to classify nuclei vs. non-nuclei image patches and the sliding-window SVM projections are efficiently computed using convolution, a readily parallelizable operation.

As noted above, the act of feature detection is embarrassingly parallel. The objective of partitioning is to ensure that the subsequent acts are optimally load balanced from a work as well as from a communication perspective. Since the Delaunay triangulation is $\mathcal{O}$ (n log n), it is desirable from a work complexity perspective for the number of points per processor to be uniformly distributed. The cost of communication is proportional to the number of points on inter-processor boundaries. To minimize the cost of communication, it is desirable to keep the number of points on inter-processor boundaries as small as possible. These goals are achieved using space-filling curves to sort the points across all processes while maintaining geometric proximity. The coordinates of each (2D) point are converted into a 1D representation using Morton encoding. The effect on the load distribution of such a partition compared with an image-based partitioning is demonstrated in FIG. 5 and a visualization of both partitions on eight processes for the location of wireless towers in the continental United States are shown in FIG. 4.

Figure 4:
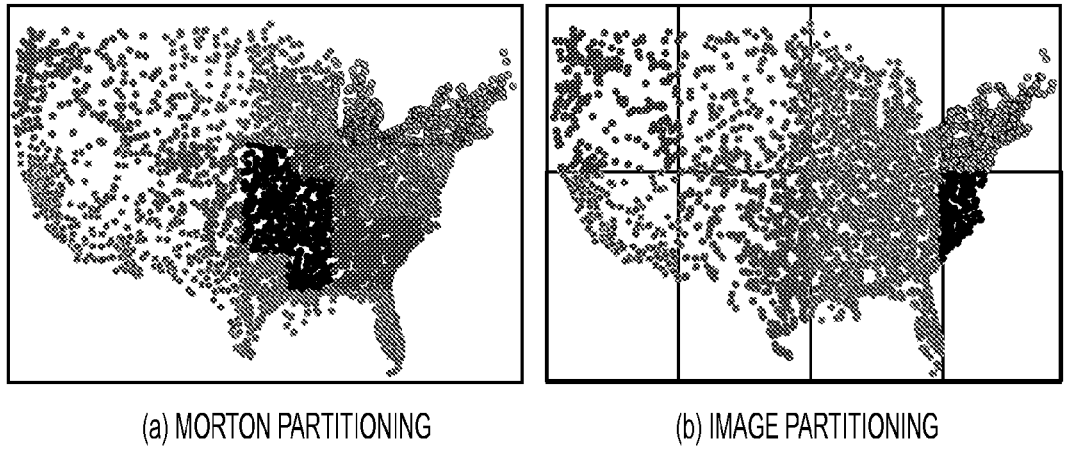
FIG. 4 shows the partitioning across 8 processes of cell tower locations in the continental United States using (a) Morton partitioning and (b) image partitioning, according to one embodiment.

As shown in FIG. 4(a), the quality of the partition across 8 processes is demonstrated using space-filling curves for the location of cell towers in the continental United States. In FIG. 4(b), the same dataset is partitioned using image-based partitioning. For rendering purposes, points from each processor are randomly sampled. As can be seen in FIG. 4, process 3, shown in brown, has a very high density of points whereas process 4, shown in black, has a significantly smaller load. Since the density of the detected features depends on the image and varies locally, it is desirable to partition using space-filling curves to maintain good load-balance during subsequent stages. The histogram of the load on individual processes for this particular partition example is presented in FIG. 5.

Figure 5:
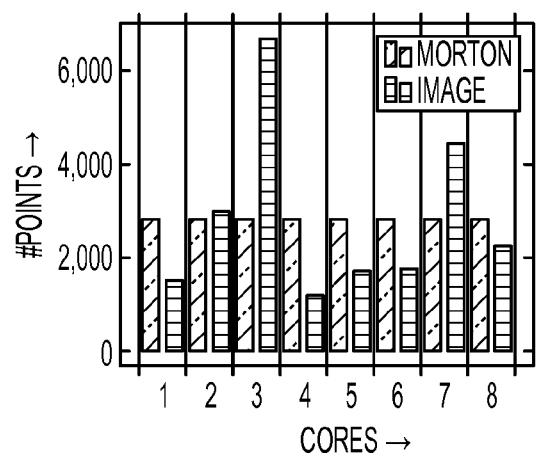
FIG. 5 shows an example histogram comparing load balancing on the 8 processors for the two types of portioning shown in FIG. 4.

The histogram shown in FIG. 5 compares the resulting load on 8 processors (e.g., processing cores or physically separate processors) for the distribution of U.S. cell towers when partitioned using space-filling curves (Morton ordering) as opposed to an image-based partitioning approach. As shown in FIG. 5, the image-based partition results in high load on processes 3 and 7 and low load on process 4.

In order to construct a Morton ordering, a discretization needs to be defined a priori. This is defined in terms of the maximum depth of the quadtree spanning the domain, $D_{max}$, which can be chosen large enough to ensure uniqueness of the input points. If the points are derived from image coordinates, the discretization is straightforward and is simply the pixel coordinate system. Each point is now represented as an integer pair (x,y), corresponding to the grid (or pixel) coordinates. The algorithm for comparing two points using their Morton encoding is given in Algorithm 2 below, which allows the points to be sorted and partitioned in parallel while maintaining geometric proximity. A variant of the sample sort algorithm is used to sort the points and the octants, which incorporates a parallel bitonic sort-to-sort of the sample elements.

---
Algorithm 2 Finding the lesser of two Morton ids, A < B
---
1: $X_i \leftarrow (A_i \text{ xor } B_i)$, $i \in \{x,y\}$
2: $e \leftarrow \arg\max_i(\lfloor \log_2(X_i) \rfloor)$
3: return $A_e < B_e$
---

The Morton ordering also allows searching for points close to inter-process boundaries. Such searches are needed to exchange points within the overlap region (FIG. 3). In order to do this, a sparse quadtree is built from only the partitioning points (i.e., the smallest points on each processor defined using Algorithm 2). This sparse quadtree ($\mathcal{O}(p)$ quadrants) defines the disjoint 2D space spanned by the points on each processor and allows fast searches to be formed. As used herein, this sparse quadtree is referred to as the partition quadtree.

In order to identify the overlap region and exchange the inter-process boundary points, the convex hull of the points on each process are first computed. In some embodiments, this is done using a sequential implementation of a variant of the monotone chain algorithm. The upper and the lower hull are computed and stored but are not merged into a single hull. In addition, the left and right hulls, which are obtained by a repeat of monotone chain algorithm with the x,y coordinates swapped, are computed. Depending on the orientation of the current processes domain with respect to that of its neighboring processes, it can be determined which boundary points need to be communicated to which processes. In some embodiments, this is done using the partition quadtree. For the simplified regular partitioning (e.g., as in the case of image-tiles), the points to be communicated from a processor (p) to its eight neighbors are:

| $\mathcal{L} \cap \mathcal{T}$ | $\mathcal{T}$ | $\mathcal{T} \cap \mathcal{R}$ |
|---|---|---|
| $\mathcal{L}$ | — | $\mathcal{R}$ |
| $\mathcal{L} \cap \mathcal{B}$ | $\mathcal{B}$ | $\mathcal{B} \cap \mathcal{R}$ | where L, R, T, a are the left, right, top, and bottom hulls, respectively.

Figure 2:
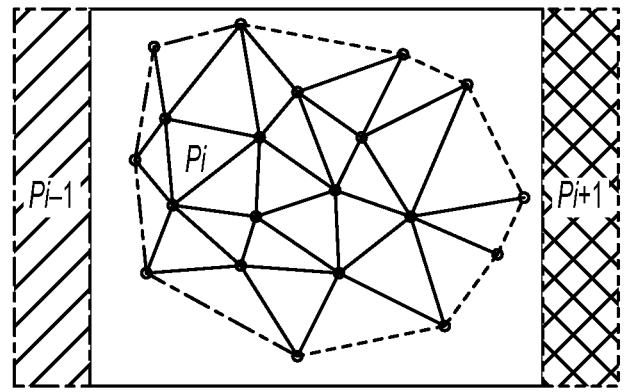
FIG. 2 shows an example RNG in which boundary points are communicated to the respective processes.

As shown in FIG. 2, the left, right, top, and bottom hull of the local points on process $p_i$ are computed. As shown in FIG. 2, the left hull is in green and the right hull is in orange. These are to be communicated to processes $p_{i-1}$ and $p_{i+1}$ respectively. For the general case, the boundary points to be communicated are in either the union or intersection of the four computed hulls.

Once which boundary points need to be communicated to which processes have been identified, the boundary points can be exchanged using MPI_Alltoallv. For large process counts (>2000), performance deterioration is observed from such global communications. Thus, since a small number of neighbors (typically 8) is expected, a switch to using point-to-point communication to exchange the inter-process boundary nodes is desirable in some embodiments. The use of point-to-point communication enables scaling at high process counts.

Computing the Delaunay triangulation of a given set of points in parallel is performed using a modified version of the DeWall algorithm since planar points are being used. The DeWall algorithm is used for the initial Delaunay triangulation prior to computing the RNG. An algorithm for parallel Delaunay triangulation is shown below in Algorithm 3:

---
Algorithm 3 par_Delaunay x, $\Gamma_x$, p
---
1: $\Gamma \leftarrow$ par_Exchange $\Gamma_x$, p
2: S ← Delaunay 0, $\Gamma$
3: S ← Delaunay S,x
4: return S
---

After partitioning and communication of the boundary layer, each process has the points it owns along with a single boundary layer of points from its neighboring processes. The combination of a process's own boundary layer along with the boundary points received from neighboring processes constitutes the overlap layer ($S^\alpha$ in FIG. 3). Each process first triangulates this overlap layer. Starting from this initial triangulation, the remaining (local) points are added to the triangulation. This results in a replication of the triangles from $S^\alpha$ across processors. Replication of the triangles is not necessary for the subsequent steps and the partitioning (i.e., assigning ownership of the triangle to a single processor) of the triangles is chosen to minimize the communication costs during the computation of the RNG.

Parallel computation of the RNG and network cycle features will now be described in more detail. It is noted that a key problem in parallelizing Urquhart's method is that the removal of edges on inter-process boundaries can result in cycles spanning processes, thereby leading to communication and synchronization issues. A solution in accordance with the present teachings handles these issues and efficiently computes the cycle order and length while removing the edges from the Delaunay triangulation. The solution includes: (1) partitioning the duplicated triangles in $S^\alpha$ to minimize communication costs; (2) marking the longest edges of all triangles; (3) merging polygons sharing marked edges (locally); and (4) for all marked edges on inter-process boundaries, exchanging polygons and merging. The steps are listed in Algorithm 4 and will be described in more detail below.

---

Algorithm 4 par_Cycles S, p

1: MarkLongestEdges S
2: Dijkstra $S^\alpha$
3: for all $\eta \in$ LongestEdge S do
4: i, j ← edge2poly $\eta$
5: $\mathcal{O}$ merged = $\mathcal{O}_i + \mathcal{O}_j - 2$
6: $C$ merged = $C_i + C_j - 2 * |\eta|$
7: end for
8: $S^{merged}$ ← par_Exchange $S^\alpha$, p
9: p' ← par_Split_Comm p
10: par_Cycles $S^{merged}$, p' (Recursive call)

---

It is desirable to avoid the presence of any "longest edges" on inter-process boundaries since these will be associated with a communication cost during the final step. Considering $S^\alpha$ in FIG. 3, then each of the triangles $\in S^\alpha$ can be partitioned to either process. The choice of this partition is going to determine which edges end up on the inter-process boundary. In order to minimize the occurrence of the longest edges on the inter-process boundary, solve for Dijkstra's shortest path on $S^\alpha$ between the end points between the processes and with edge weights set to one for the longest edge of each triangle and zero otherwise. This produces the optimal partition for all process boundaries and ensures that the minimal number of longest edges lie on inter-process boundaries. As shown in FIG. 3, this minimizes the number of polygons that have to be merged. This process is done independently on all processes. Since the overlap layer is the same on both processes, and is triangulated first in both cases, the weight and consequently the ownership is unique and the same on all processes.

Initially, all polygons are triangles from the Delaunay triangulation and therefore the polygon order is initialized to 3 and the cycle length (perimeter) is initialized by computation. All subsequent edge deletions are simply merge operations between two polygons, resulting in a new polygon of order $\mathcal{O}$ and cycle length C given by:

$$\mathcal{O}_{merged} = \mathcal{O}_i + \mathcal{O}_j - 2$$

$$C_{merged} = C_i + C_j - 2 * |e_{ij}|$$

where $e_{ij}$ is the edge that is deleted during the merge.

The number of parallel merges to be performed should be sufficiently low since this needs to be performed only for the longest-edges on the boundary and the proposed partition scheme minimizes the occurrence of such edges. For the longest-edges that remain on inter-process boundaries, the polygon and edge lists are communicated (lookup tables needed for edge2poly of Algorithm 4) to a subset of the original process and the merge is recursively performed. Only the order and cycle length need to be communicated, but other information can be communicated. The number of processes participating during the merge depends on the number of polygons to be merged. In most cases, because of the efficient partitioning scheme, it is possible to merge the boundary polygons on a single process. If the number of polygons to be merged is large, then the communicator is split to a subset of the number of processors (e.g., using MPI_Comm_Split) and the cycle length and order are recursively computed.

The following examples illustrate features in accordance with the present teachings and are provided solely by way of illustration. They are not intended to limit the scope of the appended claims or their equivalents.

The dataset shown in the left column of FIG. 1 corresponds to a case of prostate cancer obtained via light microscopy after hemotoxylin and eosin (H and E) staining and contains roughly 2000 nuclei. Nuclei detection was done using a Hessian-based algorithm. The cycles in the Urquhart graph in FIG. 1(*a*) indicate irregular cycle formations formed by tumor cells with irregular nuclei shapes. The left side of the image corresponds to a region with the most severe malignancy (Gleason grade 5) containing irregular nuclei and devoid of any glandular structures or large cycles, while the right side corresponds to Gleason grade 3, characterized by irregular glandular structures.

The data for the location of the wireless towers across the continental United States shown in the middle column of FIG. 1 is obtained directly from the FCC website. In this case, no image processing is needed to extract the feature locations. Other datasets available from the FCC include the location of US radio and TV towers.

The right column in FIG. 1 shows the simulated view of a black hole (center) in front of the Large Magellanic Cloud and contains roughly 1000 stars or starlike bright structures. Simple thresholding and non-maximum suppression are used to detect bright structures in FIG. 1(*c*). Low-intensity stars are ignored during this operation since they do not affect large cycle detection.

Figure 8:
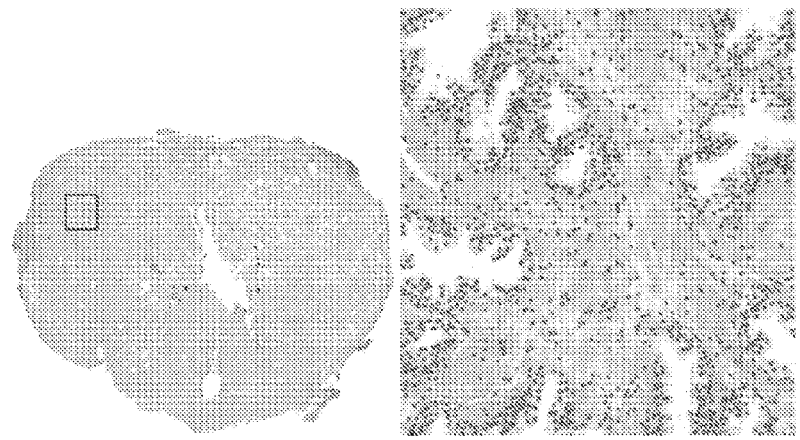
FIG. 8 shows an example prostatectomy slide with detected nuclei (blue) in inset.

A straightforward sequential algorithm for network cycle computation would first compute the pruned Delaunay networks, then apply a face-tracing algorithm, and finally compute the average cycle length/perimeter. To investigate a sequential (single-processor) version of a parallel algorithm in accordance with the present teachings, prostate cancer histopathological image data stained with H & E was obtained from a clinical collaborator. The dataset corresponded to a whole-mount prostate specimen derived from a patient who underwent a radical prostatectomy procedure. The algorithm was applied to 1 of 8 slides, with each slide corresponding to a slice obtained via a microtome. Each such slide was scanned at 10× resolution using a light microscope equipped with a robotic X-Y stage for slide-scanning. As shown in FIG. 8, the whole slide used for the computational experiments had a native size of roughly 64000×47000 pixels, where each pixel was 0.64×0.64 microns in size. Dynamic contrast enhanced magnetic resonance (DCE-MR) and T2 weighted-MR scans for this patient are available. The sequential (single-processor) version of a parallel algorithm in accordance with the present teachings offers a speed-up factor of over 30 in comparison to the straightforward algorithm for 6600 nuclei detected from an 1360×1024 image patch derived from the prostate histopathology slide described above.

For embodiments in which the input is an image, the image can be partitioned into equal chunks (possibly with an overlap) across the processes. While this may be a good choice for feature extraction algorithms that have a run time complexity dependent on the image dimensions, it is a poor choice for algorithms that operate on the extracted features. Since the features are data dependent, the number of features obtained from equally sized image chunks are not guaranteed to be equal. To highlight this issue, an experiment was conducted (FIGS. 4 and 5) using U.S. wireless-tower data, and the load imbalance for the proposed partition method compared to the image-based partition approach was evaluated. For a total of 23,153 towers non-uniformly distributed over the United States, the distribution of this dataset over 8 processors for both approaches is shown in FIG. 5. A sparse visualization of the resulting partition from both approaches is shown in FIG. 4. Using the proposed Morton-order based partitioning results in near uniform distribution while the image-based partition resulted in a load imbalance factor of approximately 6.

As further described below, a series of scalability tests were performed. While reporting scalability results, total runtimes are presented in a stacked manner breaking up the total runtime into three major components: (1) partition (dividing the points across the processes and communicating the shared boundary layer); (2) meshing (Delaunay triangulation and computing the edge to triangle mappings); and (3) Urquhart (computing the RNG and cycle statistics). As further described below, parallel algorithms in accordance with the present teachings demonstrate excellent fixed-size (strong) and isogranularity (weak) scalability using large datasets (up to 13 billion points) on 131 K cores.

Figure 9:
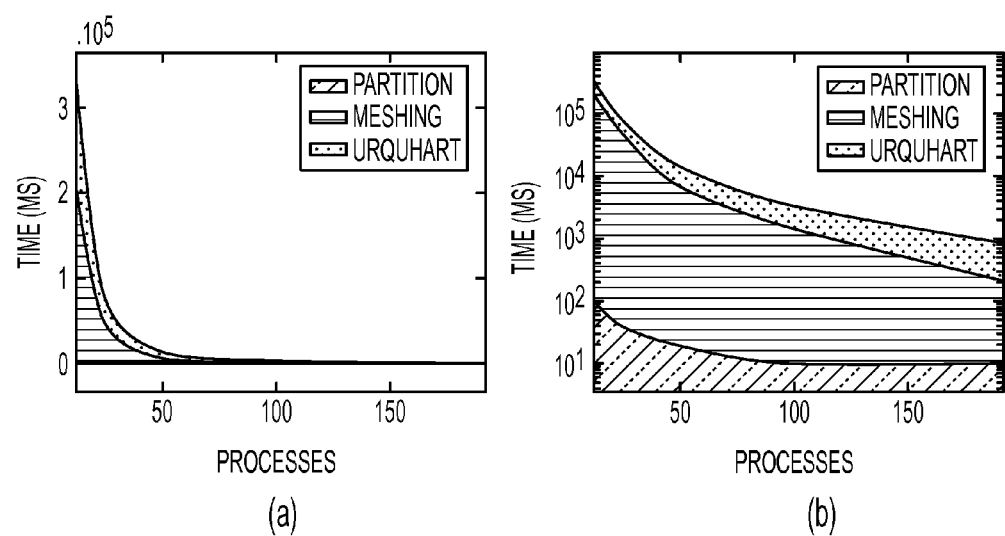
FIG. 9 shows example data for a fixed-size scalability study with 1.5 million nuclei on the Lonestar cluster for process count from 24-384 on both regular and a semi-logarithmic scale.
Figure 10:
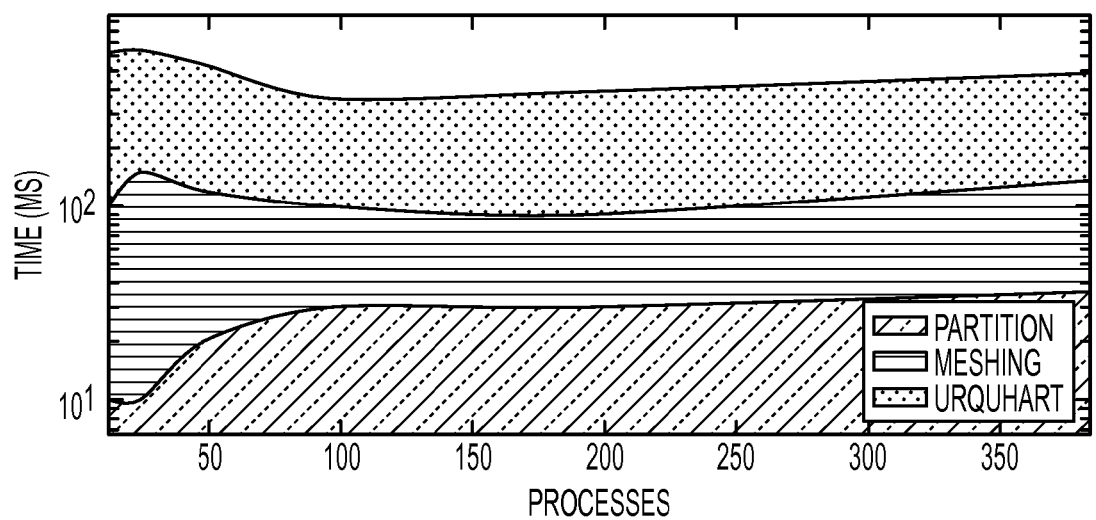
FIG. 10 shows example data for an isogranular scalability study with a grain size of 10,000 nuclei per process on the Lonestar cluster for process counts till 384 shown on a semi-logarithmic scale.

A first series of scalability tests were performed on the Texas Advanced Computing Center's Lonestar cluster. All algorithms were implemented using C++ using the MPI library for parallelization. Fixed-sized (strong) scalability tests were performed using data described above in connection with the sample in FIG. 8. This slice contained a total of 1.5 million nuclei from which the network cycle features were computed for process counts up to 196. The fixed scalability metrics are shown in FIG. 9. As shown in FIG. 9, the method shows excellent scalability allowing the problem to be solved in approximately 1 second using 196 processes. An isogranular (weak) scalability study was also performed on this sample by keeping the number of nuclei per process fixed at 10,000 (the nuclei locations were randomly distributed over a unit square) and observing performance for increasing problem sizes and number of processes. These are plotted in FIG. 10. As shown in FIG. 10, near linear isogranular scalability is achieved, thereby indicating an effective parallelization of the problem and the ability to solve even larger problems in approximately 1 second by increasing the number of processes.

A second series of scalability experiments were carried out on "Jaguar," the ORNL Cray XK6 system that has a total of 299,008 AMD Opteron 6200-series cores and the Gemini interconnect system. The largest runs reported in this work used a total of 131,072 cores using one MPI process per core. All algorithms were implemented using C++ using the MPI library for parallelization.

Figure 6:
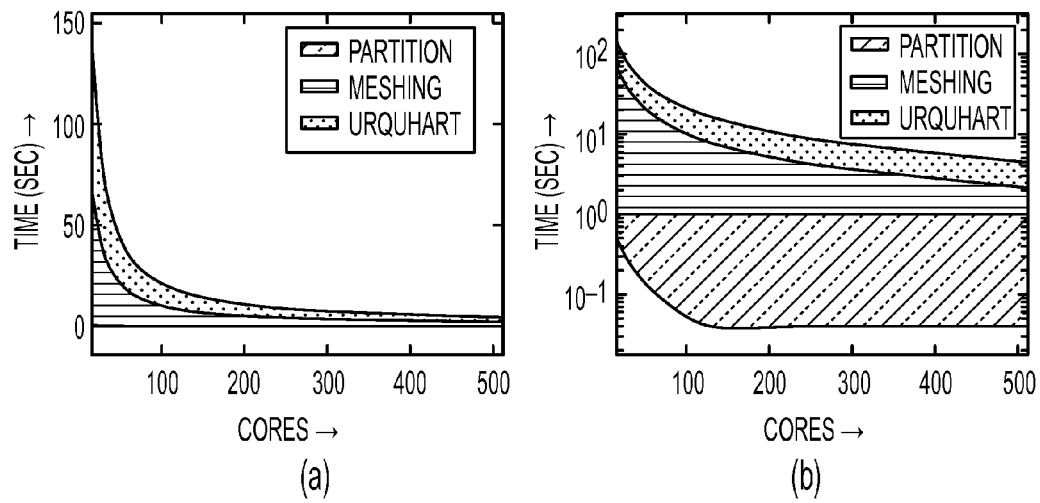
FIG. 6 shows example data for a fixed-size scalability study with 6.5 million points on "Jaguar" for process count from 16-256 on both a regular and semi-logarithmic scale.

A point set with approximately 6.5 million points was generated for the strong scaling experiments. Network cycle lengths were computed for process counts in the range 16-512. The fixed scalability metrics are plotted in FIG. 6. The fixed-size scalability with 6.5 million points on "Jaguar" for process counts from 16-256 is shown on both regular and a semi-logarithmic scale. The overall time is split into the time for partitioning the points using space filling curves (partition), the time to mesh the points using Delaunay triangulation and to build the edge to triangle lookup tables (meshing), and the time to compute the relative neighborhood graph and compute the cycle length and order (Urquhart). As shown by FIG. 6, the proposed method shows excellent scalability. The sustained reduction in total computation time for a 32-fold increase in process count indicates good load balancing and low communication costs due to the use of point-to-point communication. Moreover, the extremely low overhead of partitioning the points using the Morton ordering justifies the additional work to obtain good load balance.

Figure 7:
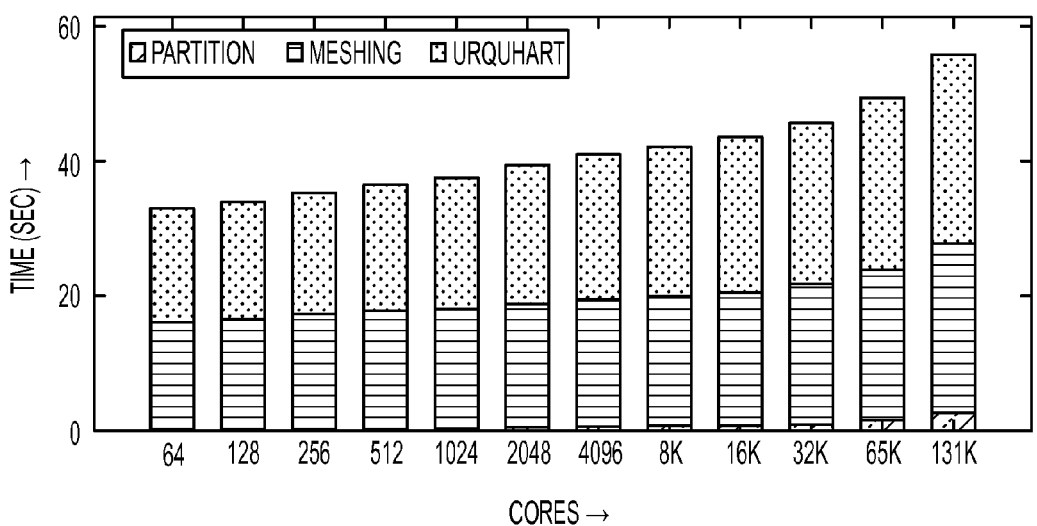
FIG. 7 shows example data for an isogranular scalability study with a grain size of 100,000 points per process on "Jaguar' for process counts till 131 K on a semi-logarithmic scale.

Isogranular scalability studies were also performed by keeping the number of points per process fixed at 100,000 (the points were randomly distributed over the unit square) and observing performance for increasing problem sizes and number of processes. These data are plotted in FIG. 7. The isogranular scalability with a grain size of 100,000 points per process on "Jaguar" for process counts till 131 K is shown on a semi-logarithmic scale. The overall time is split into the time for partitioning the points using space filling curves (partition), the time to mesh the points using Delaunay triangulation and to build the edge-to-triangle lookup tables (meshing), and the time to compute the relative neighborhood graph and compute the cycle length and order (Urquhart). The first two stages have a time complexity of $\mathcal{O}$ (N/p log N), and the third stage has a time complexity of $\mathcal{O}$ (N/p). Therefore the isogranular scalability is not flat. Since the problem size and the number of processes is increased linearly, the gradual rise in run-time is expected. Near optimal isogranular scalability is achieved indicating an effective parallelization of the problem and the ability to solve even larger problems by increasing the number of processes. For a 2048-fold increase in problem size, the run-time increases by less than a factor of two.

It is to be understood that elements and features of the various representative embodiments described below may be combined in different ways to produce new embodiments that likewise fall within the scope of the present teachings.

Figure 11:
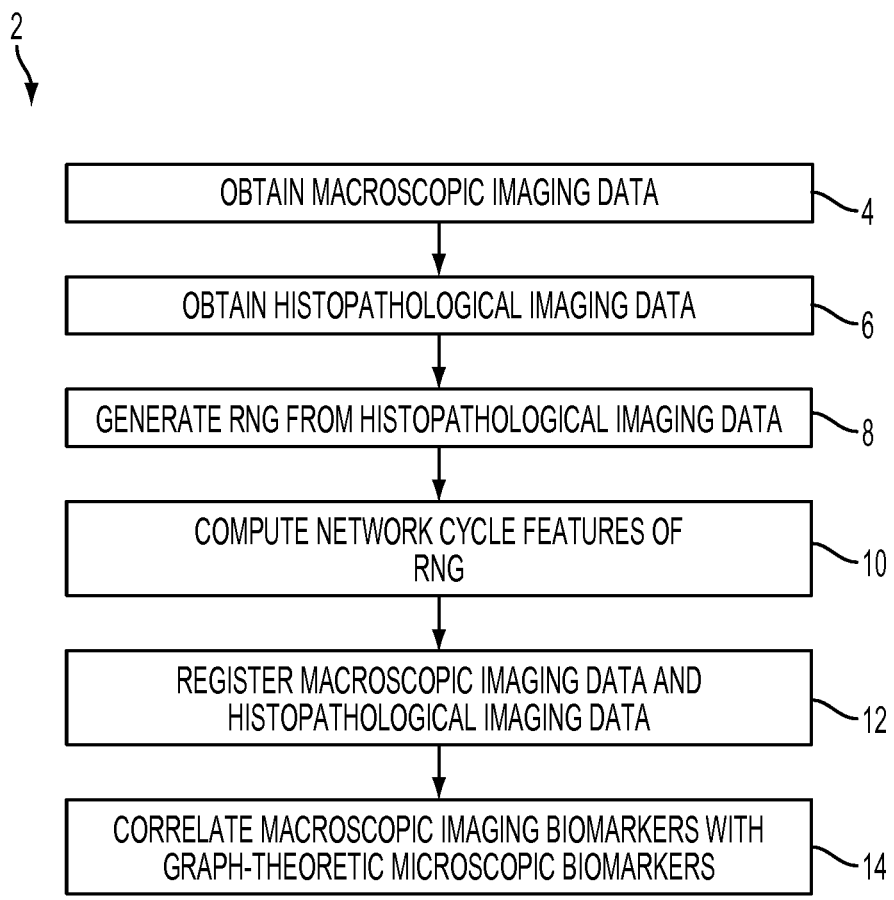
FIG. 11 is a flow chart of a representative method for analyzing biomedical data.

As shown in the flow chart of FIG. 11, a first method 2 for analyzing biomedical data embodying features of the present teachings includes (a) obtaining macroscopic imaging data 4; (b) obtaining histopathological imaging data 6; (c) generating a relative neighborhood graph (RNG) from the histopathological imaging data 8; (d) computing one or a plurality of network cycle features of the RNG 10; (e) registering the macroscopic imaging data and the histopathological imaging data 12; and (f) correlating the macroscopic imaging data and the network cycle features 14.

In some embodiments, the network cycle features computed in act 10 are selected from the group consisting of cycle order, cycle perimeter, and a combination thereof. In some embodiments, generation of the RNG from the histopathological imaging data 8 and/or computation of the network cycle features of the RNG 10 comprises parallel computation. In some embodiments, both generation of the RNG from the histopathological imaging data 8 as well as computation of the network cycle features of the RNG 10 comprise parallel computation. In some embodiments, methods in accordance with the present teachings include executing a parallel algorithm stored on a non-transient computer-readable medium to compute network cycle features 10 of a relative neighborhood graph derived from the histopathological imaging data 8.

It is to be understood that the relative ordering of some acts shown in the flow chart of FIG. 11 is meant to be representative rather than limiting, and that alternative sequences may be followed. Moreover, it is likewise to be understood that additional, different, or fewer acts may be provided. By way of example, the first act shown in FIG. 11 need not be obtaining macroscopic imaging data 2. Instead, in alternative embodiments, obtaining macroscopic imaging data 2 can occur after and/or substantially simultaneously with one or more of acts 6, 8, and 10 (although, as presently preferred, the obtaining of the macroscopic imaging data 2 occurs prior to registering the macroscopic imaging data and the histopathological imaging data 12). Similarly, the fifth act shown in FIG. 11 need not be the registering of the macroscopic imaging data and the histopathological imaging data 12. Instead, in other embodiments, the registering can occur before, after and/or substantially simultaneously with one or more of acts 8 and 10.

In still other embodiments, the acts performed in a method in accordance with the present teachings are all directed within a microscopic (e.g., histopathological) domain, such that acts 4, 12, and 14 shown in FIG. 11 are not performed. By way of example, in some embodiments, which can be used to enable rapid cancer detection and/or Gleason scoring of a biopsy slide, a method in accordance with the present teachings includes acts 6, 8, and 10 from FIG. 11 but does not include acts 4, 12, and 14. In some embodiments, such a method can further include at least one additional act (not shown in FIG. 11) selected from the group consisting of (a) predicting a presence and/or severity of a disease using the network cycle features, (b) correlating graph-theoretic microscopic biomarkers (e.g., the network cycle features) with the presence and/or severity of the disease, and (c) a combination thereof.

In still other embodiments, the acts performed in a method in accordance with the present teachings are all directed within a macroscopic or astronomic domain. In such embodiments, acts 6, 12, and 14 in FIG. 11 are not performed, and act 8 is modified—for example, into a new act 9 (not shown)—wherein the ANG is generated from macroscopic or astronomic imaging data (as opposed to histopathological) imaging data. By way of example, such embodiments can be used to identify areas with low cellular coverage (macroscopic domain) or potential candidates for black holes in space (astronomic domain). In the field of wireless networking, a method in accordance with the present teachings can further include at least one additional act selected from the group consisting of (a) predicting a presence and/or degree of insufficient cellular coverage using the network cycle features, (b) correlating the network cycle features with the presence and/or degree of insufficient cellular coverage, and (c) a combination thereof. In the field of astronomy, a method in accordance with the present teachings can further include at least one additional act selected from the group consisting of (a) predicting a presence and/or size of a black hole using the network cycle features, (b) correlating the network cycle features with the presence and/or size of a black hole, and (c) a combination thereof.

Figure 12:
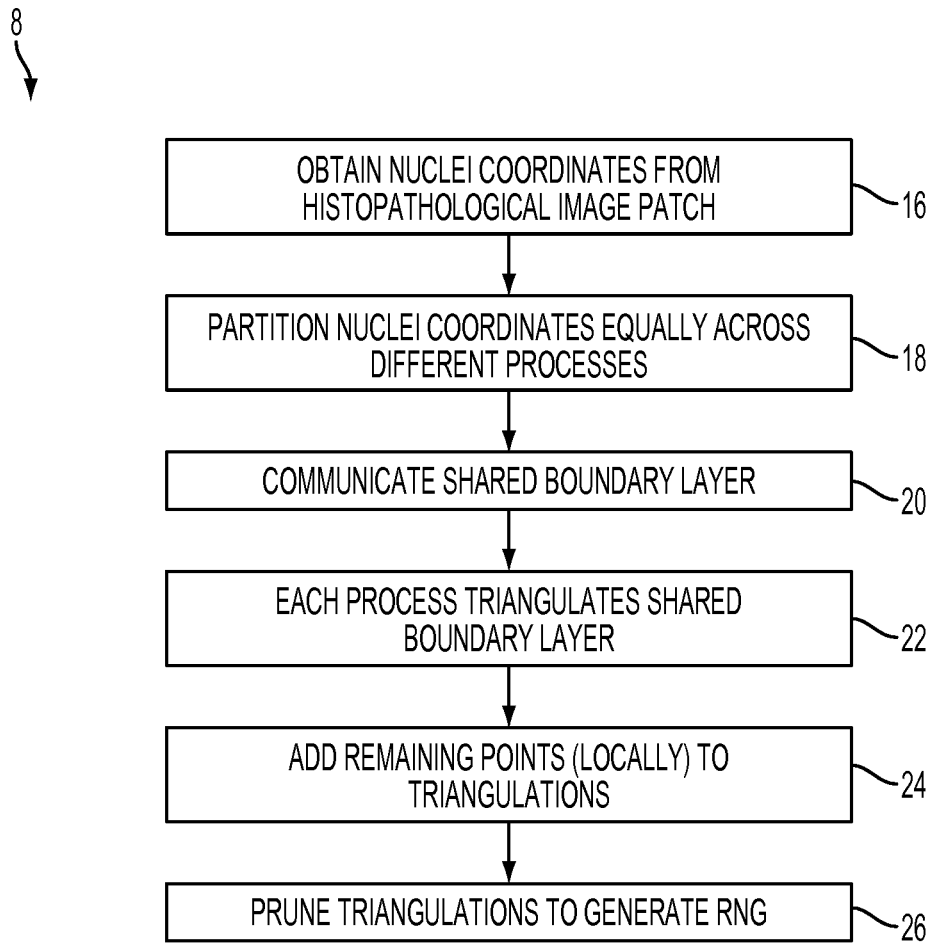
FIG. 12 is a flow chart of a representative method for generating a relative neighborhood graph from histopathological imaging data.

FIG. 12 is a flow chart showing representative acts in the generation of an RNG from histopathological imaging data 8. It is to be understood that the relative ordering of some acts shown in the flow chart of FIG. 12 is meant to be representative rather than limiting, and that alternative sequences may be followed. Moreover, it is likewise to be understood that additional, different, or fewer acts may be provided. By way of example, as shown in FIG. 12, the generation of the RNG 8 includes: (a) obtaining nuclei coordinates from a histopathological image patch 16; (b) partitioning the nuclei coordinates equally across different processes 18; (c) communicating a shared boundary layer 20; (d) triangulation of the shared boundary layer by each process 22; (e) addition of remaining (local) points to the respective triangulations of each process 24; and (f) pruning of the triangulations to generate the RNG 26.

In some embodiments, the partitioning of the nuclei coordinates equally across different processes 18 comprises quadtree-based partitioning and, in some embodiments, Morton ordering of the nuclei coordinates to optimize load balance. In some embodiments, the triangulation comprises Delaunay triangulation. Other approaches may be used.

Figure 13:
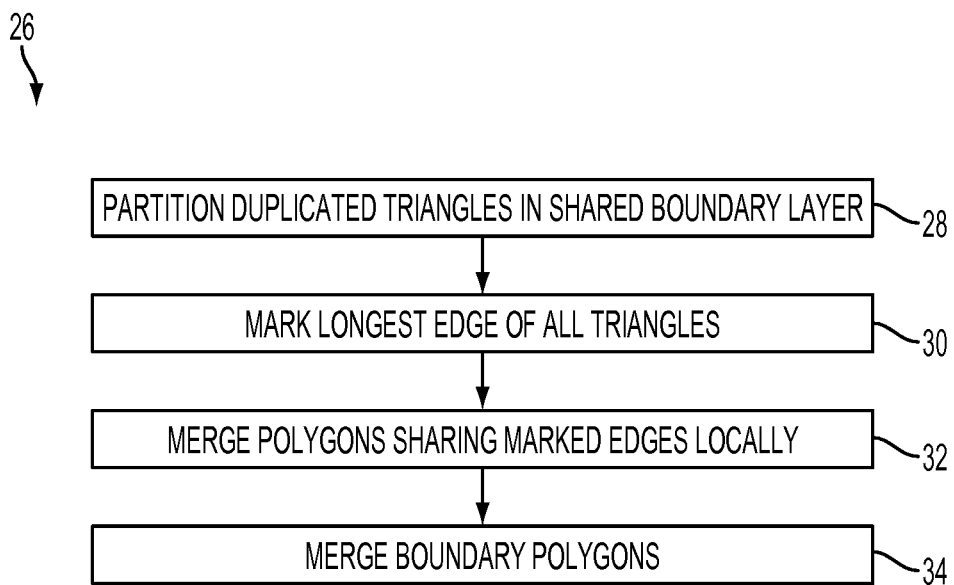
FIG. 13 is a flow chart of a representative method for pruning triangulations of parallel processes to generate a relative neighborhood graph.

In some embodiments, the pruning comprises an Urquhart approximation to a RNG, which is obtained by removing the longest edge from every triangle of a Delaunay network. In some embodiments, the pruning comprises parallel computation. FIG. 13 is a flow chart showing representative acts in the pruning of the triangulations to generate the RNG 26. It is to be understood that the relative ordering of some acts shown in the flow chart of FIG. 13 is meant to be representative rather than limiting, and that alternative sequences may be followed. Moreover, it is likewise to be understood that additional, different, or fewer acts may be provided. By way of example, as shown in FIG. 13, the pruning includes (a) partitioning duplicated triangles in the shared boundary layer 28; (b) marking a longest edge of each the triangles 30; (c) merging polygons sharing marked edges locally 32; and (d) merging boundary polygons 34.

In some embodiments, the partitioning of duplicated triangles in the shared boundary layer 28 comprises solving for Dijkstra's shortest path on the shared boundary layer between the end points between the processes. In some embodiments, the marking of the longest edge of each the triangles 30 comprises setting the edge weight to 1 for the longest edge of each triangle and 0 for all other edges. In some embodiments, for the longest edges that remain on inter-process boundaries, the polygon and edge lists are communicated to a subset of the original process and the merging of the boundary polygons 34 is performed recursively.

The type of biomedical data analyzed in accordance with the present teachings is not restricted and, as presently contemplated, all manner of biomedical data can be studied. In some embodiments, the biomedical data are indicative of whether a disease is present and/or a severity of the disease. In some embodiments, the disease comprises cancer. By way of example, representative types of cancer that can be studied and analyzed in accordance with the present teachings include but are not limited to prostate cancer, breast cancer, lung cancer, liver cancer, pancreatic cancer, brain cancer, bladder cancer, cervical cancer, colon cancer, skin cancer, renal cell cancer, ovarian cancer, testicular cancer, and the like, and combinations thereof. In some embodiments, the disease comprises prostate cancer. In other embodiments, the disease comprises breast cancer.

The type of macroscopic imaging data used for analyzing biomedical data in accordance with the present teachings is not restricted and, as presently contemplated, all manner of imaging techniques presently known and to be discovered in the future can be used in accordance with these teachings. By way of example, representative types of imaging data include but are not limited to magnetic resonance data, computed tomography data, positron emission tomography data, single photon emission tomography data, ultrasound data, and the like, and combinations thereof. In some embodiments, the macroscopic imaging data comprise DCE-MR data.

The registering of the macroscopic imaging data and the histopathological imaging data 12 can be accomplished by various methodologies including but not limited to the approach described in United States Patent Application Publication No. US 2011/0040169 A1, which is assigned to the assignee of the present application. The entire contents of this publication are hereby incorporated by reference, except that in the event of any inconsistent disclosure or definition from the present specification, the disclosure or definition herein shall be deemed to prevail. As described in US 2011/0040169 A1, macroscopic imaging data (e.g., such as CT, MR, PET, or SPECT data) is aligned with microscopic imaging data (e.g., obtained from at least a portion of the same tissue) through intermediate data (e.g., photographic data), which is acquired at an intermediary stage of a process of preparing tissue for microscopic scan. The macroscopic and microscopic data are registered to the intermediary photographic data, after which the spatial relationship between the macroscopic and microscopic data is known and may be used for imaging and/or quantification.

As noted above, in some embodiments, methods in accordance with the present teachings are restricted to a microscopic (e.g., histopathological) domain, such that acts 4, 12, and 14 shown in FIG. 11 are unnecessary. In such embodiments, a method for analyzing biomedical data in accordance with the present teachings includes: (a) obtaining histopathological imaging data; (b) executing a parallel algorithm stored on a non-transient computer-readable medium to compute one or a plurality of network cycle features of a relative neighborhood graph derived from the histopathological imaging data; and (c) doing one or both of the following: (I) predicting a presence and/or severity of a disease using the network cycle features, and (ii) correlating graph-theoretic microscopic biomarkers (e.g., the network cycle features) with the presence and/or severity of the disease. These embodiments can be used, for example, to enable rapid cancer detection and/or Gleason scoring of a biopsy slide (e.g., a prostate biopsy slide, a breast biopsy slide, or the like).

Figure 14:
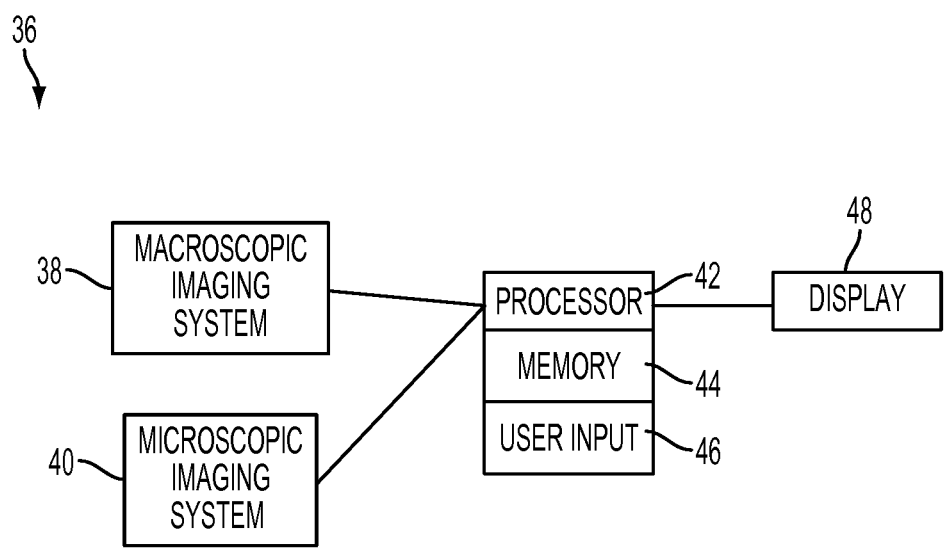
FIG. 14 is a block diagram of a representative system for analyzing biomedical data.

FIG. 14 shows a block diagram of a representative system 36 for analyzing biomedical data that embodies features of the present teachings. As shown in FIG. 14, the system 36 includes: a memory 44 operable to store macroscopic imaging data provided by a macroscopic imaging system 38 and histopathological imaging data provided by a microscopic imaging system 40; a processor 42 configured to generate a relative neighborhood graph from the histopathological imaging data by parallel computation, compute one or a plurality of network cycle features (e.g., cycle order and/or cycle perimeter) of the relative neighborhood graph by parallel computation, and correlate the macroscopic imaging data and the network cycle features; and a display 48 operable to display an analysis result derived from correlation of the macroscopic imaging data and the network cycle features. In some embodiments, the analysis result is selected from the group consisting of RNGs, shared boundary layers, cycle orders, cycle perimeters, detected nuclei in a whole-mount slide, Gleason grades, and the like, and combinations thereof. In some embodiments, the display 48 is further operable to display identifying data and/or patient data associated with a given sample. In some embodiments, the system 36 further includes a user input 46 operable to receive input from a system user.

The type of macroscopic imaging system 38 used to provide macroscopic imaging data to processor 42 in accordance with the present teachings is not restricted and, as presently contemplated, all manner of imaging systems presently known and to be discovered in the future can be used in accordance with these teachings. By way of example, representative types of macroscopic imaging systems include but are not limited to magnetic resonance imaging, computed tomography, positron emission tomography, single photon emission tomography, ultrasound, and the like, and combinations thereof. In some embodiments, the macroscopic imaging system comprises dynamic contrast enhanced magnetic resonance imaging.

A computer readable storage medium embodying features of the present teachings has stored therein data representing instructions executable by a programmed processor for biomedical study. In some embodiments, the storage medium includes instructions for: generating a relative neighborhood graph from histopathological imaging data by parallel computation; computing one or a plurality of network cycle features of the relative neighborhood graph by parallel computation; and correlating the macroscopic imaging data and the network cycle features.

In some embodiments, the storage medium further comprises instructions for (a) quadtree-based partitioning of nuclei coordinates obtained from the histopathological imaging data across a plurality of processes; (b) Morton ordering of the nuclei coordinates to optimize load balance; (c) creation of a shared boundary layer, wherein each of the processes Delaunay triangulates the shared boundary layer, and wherein remaining local points are added to each process's respective triangulations; and/or (d) pruning the triangulations to generate the relative neighborhood graph.

In some embodiments, the storage medium further comprises instructions for (e) preparing an Urquhart graph from the Delaunay triangulations; (f) partitioning duplicated triangles in the shared boundary layer; (g) marking a longest edge of each triangle; (h) merging polygons sharing marked edges locally; and/or (i) merging boundary polygons.

In some embodiments, the systems, methods, engines, and descriptions may be encoded in a non-transitory signal bearing storage medium, a computer-readable medium, and/or may comprise logic stored in a memory that may be accessible through an interface and executable by one or more processors. Some signal-bearing storage media or computer-readable media comprise a memory that is unitary or separate (e.g., local or remote) from an enabled device. If the descriptions or methods are performed by software, the software and/or logic may reside in a memory resident to or interfaced with one or more microprocessors, signal processors, devices, or controllers that may support a tangible, aural, or visual communication interface (e.g., to a display), wireless communication interface, or wireless system.

The memory may retain an ordered listing of executable instructions for implementing logical functions. A logical function may be implemented through digital circuitry, through source code, and/or through analog circuitry. A "computer-readable storage medium," "machine-readable medium," "propagated-signal" medium and/or "signal-bearing medium" may comprise a non-transitory medium that stores, communicates, propagates, and/or transports software or data for use by or in connection with an instruction executable system, apparatus, or device. The machine-readable medium may selectively be, but is not limited to, an electronic, magnetic, optical, electromagnetic, infrared, or semiconductor system, apparatus, device, or propagation medium. Representative examples of machine-readable media include but are not limited to an electrical connection having one or more wires; a portable magnetic or optical disk; a volatile memory, such as a Random Access Memory (RAM), a Read-Only Memory (ROM), an Erasable Programmable Read-Only Memory (EPROM or Flash memory), or an optical fiber; and the like; and combinations thereof. A machine-readable medium may also include a tangible medium, as the software may be electronically stored as an image or in another format (e.g., through an optical scan), then compiled, and/or interpreted or otherwise processed. The processed medium may then be stored in a memory or database accessible by a database engine that provides access to a database management system.

As shown in FIG. 14, the system 36 includes a memory 44, a microscopic imaging system 40, a macroscopic imaging system 38, a user input 46, a processor 42, and a display 48. It is to be understood, however, that additional, different, or fewer components may be provided. By way of example, a network or network connection can be provided, such as for networking with a medical imaging network or data archival system. As another example, additional macroscopic and/or microscopic imaging systems can be provided. In some embodiments, the macroscopic and/or microscopic imaging data are stored in the memory 44.

In some embodiments, the processor 42, user input 46, and display 48 are part of a medical imaging system, such as a diagnostic or therapy ultrasound, fluoroscopy, x-ray, computed tomography, magnetic resonance, positron emission, or the like. In some embodiments, the processor 42, user input 46, and display 48 are part of an archival and/or image processing system, such as associated with a medical records database workstation or server. In some embodiments, the processor 42, user input 46, and display 48 are a personal computer, such as a desktop or laptop, a workstation, a server, a network, or combinations thereof. In some embodiments, the memory 44 is part of the workstation or system or is a remote database or memory medium.

In some embodiments, the user input 46 comprises a keyboard, button, slider, knob, touch screen, touch pad, mouse, trackball, or the like, and combinations thereof, or other now known or later developed user input device. The user input 46 receives user indication of interaction with a user interface. The user may select data, control rendering, control imaging, navigate, cause calculation, search, or perform other functions associated with use, imaging, and/or modeling of macroscopic and/or microscopic imaging data.

In some embodiments, the memory 44 is a graphics processing memory, a video random access memory, a random access memory, system memory, random access memory, cache memory, hard drive, optical media, magnetic media, flash drive, buffer, database, server memory, and the like, and combinations thereof, or other now known or later developed memory device for storing data or video information. In some embodiments, the memory 44 is part of an imaging system, part of a computer associated with the processor 42, part of a database, part of an archival system, part of another system, or a standalone device.

In some embodiments, the memory 44 stores one or more datasets representing a two or three-dimensional tissue volume. The tissue volume is a region of the patient or animal, such as a region within the chest, abdomen, leg, head, arm, or combinations thereof, or a region of biopsied or harvested tissue. The tissue volume is a region scanned by a medical imaging modality. Different modalities or even scans with a same modality may be of a same or different size regions with or without overlap. The data may represent planar (2D), linear (1D), point, or temporal (4D) regions for one or more datasets.

In some embodiments, at least one set of data is data from a microscopic imaging source, such as the microscopic imaging system 40. The microscopic imaging system 40 can be a microscope, confocal microscope system, or other now known or later developed microscopic imaging system.

In some embodiments, the processor 42 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for determining position, modeling, and/or generating images. In some embodiments, the processor 42 is a single device or multiple devices operating in serial, parallel, or separately. In some embodiments, the processor 42 may be a main processor of a computer, such as a laptop or desktop computer, or may be a processor for handling some tasks in a larger system, such as in an imaging system.

The processor 42 loads the data and, in some embodiments, the processor 42 also loads the microscopic imaging data and macroscopic imaging data for registering 12. For embodiments in which registration is accomplished using a methodology as described in US 2011/0040169 A1, the processor 42 further loads intermediary data. The spatial alignment in rotation, translation, and/or warping of the macroscopic and microscopic data is determined. In some embodiments, the registering 12 is performed automatically by processor 42. In other embodiments, the registration is performed semi-automatically based on instructions and/or decisions from a user that are entered through user input 46.

In some embodiments, the processor 42 is operable to render an image as a function of the registered data that can be displayed on display 48. Any type of rendering may be used, such as surface rendering, multi-planar reconstruction, projection rendering, and/or generation of an image representing a plane. For example, the image can be generated as a rendering of or an arbitrary plane through the tissue volume. The image includes values for pixel locations where each of the values is a function of one or both of macroscopic and microscopic data.

In some embodiments, the image is rendered based on user selection of the type of data. Where datasets corresponding to different or no structural or functional labeling are available, the user may select the dataset to be used for imaging. The dataset may be the same or different from the data used for registration.

Spatially aligned data may be combined, such as by summing, averaging, alpha blending, maximum selection, minimum selection or other process. In some embodiments, the combined data set is rendered as a three-dimensional representation. Separate renderings may be used, such as laying a microscopic rendering over a macroscopic rendering. The combination provides feedback about relative position of the microscopic data to the larger macroscopically scanned region.

The processor 42 may calculate quantities. Modeling and/or machine learning associated with the registered data may be performed by the processor 42.

In some embodiments, the display 48 is a monitor, LCD, projector, plasma display, CRT, printer, combinations thereof, or other now known or later developed devise for outputting visual information. The display 48 receives images, graphics, or other information from the processor 42, memory 44, microscopic imaging system 40, and/or macroscopic imaging system 38.

In conclusion, scalable parallel algorithms for the computation of relative neighborhood graphs and associated cycle statistics, which will be of interest in a wide array of applications, have been discovered and are described herein. Among other advantages, the scalable parallel algorithms described herein will permit for the first time a multi-patient, multi-slice study of correlations between macroscopic and individual microscopic biomarkers (as opposed to simply a pathologist's score).

The entire contents of each and every patent and non-patent publication cited herein are hereby incorporated by reference, except that in the event of any inconsistent disclosure or definition from the present specification, the disclosure or definition herein shall be deemed to prevail.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent—and that such new combinations are to be understood as forming a part of the present specification.

The invention claimed is:

1. A method for analyzing biomedical data comprising:
   obtaining macroscopic imaging data;
   obtaining histopathological imaging data;
   generating a relative neighborhood graph from the histopathological imaging data by parallel computation;
   executing a parallel algorithm stored on a non-transient computer-readable medium to compute one or a plurality of network cycle features of an Urquhart-approximation of the relative neighborhood graph;
   quadtree-based partitioning of nuclei coordinates obtained from the histopathological imaging data across a plurality of processes;
   Morton ordering of the nuclei coordinates to optimize load balance;
   creating a shared boundary layer, wherein each of the processes Delaunay triangulates the shared boundary layer, and wherein remaining local points are added to each process's respective triangulations;
   pruning the triangulations to generate the relative neighborhood graph;
   registering the macroscopic imaging data and the histopathological imaging data; and
   correlating the macroscopic imaging data and the network cycle features.

2. The method of claim 1 wherein the network cycle features are selected from the group consisting of cycle order, cycle perimeter, and a combination thereof.

3. The method of claim 1 further comprising:
   partitioning duplicated triangles in the shared boundary layer;
   marking a longest edge of each the triangles;
   merging polygons sharing marked edges locally; and
   merging boundary polygons.

4. The method of claim 1 wherein the biomedical data are indicative of whether a disease is present and/or a severity of the disease.

5. The method of claim 4 wherein the disease comprises cancer.

6. The method of claim 4 wherein the disease comprises prostate cancer.

7. The method of claim 1 wherein the macroscopic imaging data are selected from the group consisting of magnetic resonance data, computed tomography data, positron emission tomography data, single photon emission tomography data, and combinations thereof.

8. The method of claim 1 wherein the macroscopic imaging data comprise dynamic contrast enhanced magnetic resonance data.

9. A system for analyzing biomedical data comprising:
   a memory operable to store macroscopic imaging data and histopathological imaging data;
   a processor operable to (a) generate an Urquhart-approximation of a relative neighborhood graph from the histopathological imaging data by parallel computation; (b) compute one or a plurality of network cycle features of the relative neighborhood graph by parallel computation; (c) quadtree-based partition nuclei coordinates obtained from the histopathological imaging data across a plurality of processes; (d) Morton order the nuclei coordinates to optimize load balance; (e) create a shared boundary layer, wherein each of the processes Delaunay triangulates the shared boundary layer, and wherein remaining local points are added to each process's respective triangulations; (f) prune the triangulations to generate the relative neighborhood graph; and (g) correlate the macroscopic imaging data and the network cycle features; and
   a display operable to display an analysis result derived from correlation of the macroscopic imaging data and the network cycle features.

10. The system of claim 9 wherein the network cycle features are selected from the group consisting of cycle order, cycle perimeter, and a combination thereof.

11. The system of claim 9 further comprising a user input operable to receive input from a system user.

12. The system of claim 9 wherein the biomedical data are indicative of whether a disease is present and/or a severity of the disease.

13. The system of claim 12 wherein the disease comprises cancer.

14. The system of claim 12 wherein the disease comprises prostate cancer.

15. The system of claim 9 wherein the macroscopic imaging data are selected from the group consisting of magnetic resonance data, computed tomography data, positron emission tomography data, single photon emission tomography data, and combinations thereof.

16. The system of claim 9 wherein the macroscopic imaging data comprise dynamic contrast enhanced magnetic resonance data.

17. A non-transitory computer readable storage medium having stored therein data representing instructions executable by a programmed processor for biomedical study, the storage medium comprising instructions for:
   generating an Urquhart-approximation of a relative neighborhood graph from histopathological imaging data by parallel computation;
   computing one or a plurality of network cycle features of the relative neighborhood graph by parallel computation;
   quadtree-based partitioning of nuclei coordinates obtained from the histopathological imaging data across a plurality of processes;
   Morton ordering of the nuclei coordinates to optimize load balance;
   creating a shared boundary layer, wherein each of the processes Delaunay triangulates the shared boundary layer, and wherein remaining local points are added to each process's respective triangulations;
   pruning the triangulations to generate the relative neighborhood graph; and
   correlating the macroscopic imaging data and the network cycle features.

18. The non-transitory computer readable storage medium or claim 17 wherein the storage medium further comprises instructions for:
   preparing an Urquhart graph from the Delaunay triangulations;

partitioning duplicated triangles in the shared boundary layer;
marking a longest edge of each triangle;
merging polygons sharing marked edges locally; and
merging boundary polygons.

19. A method for analyzing biomedical data comprising:
(a) obtaining histopathological imaging data;
(b) generating a relative neighborhood graph from the histopathological imaging data by parallel computation;
(c) executing a parallel algorithm stored on a non-transient computer-readable medium to compute one or a plurality of network cycle features of an Urquhart-approximation of the relative neighborhood graph;
(d) quadtree-based partitioning of nuclei coordinates obtained from the histopathological imaging data across a plurality of processes;
(e) Morton ordering of the nuclei coordinates to optimize load balance;
(f) creating a shared boundary layer, wherein each of the processes Delaunay triangulates the shared boundary layer, and wherein remaining local points are added to each process's respective triangulations;
(g) pruning the triangulations to generate the relative neighborhood graph; and
(h) predicting a presence and/or severity of a disease using the network cycle features, and/or correlating graph-theoretic microscopic biomarkers with the presence and/or severity of the disease.

20. The method of claim 19 wherein the disease comprises cancer.

* * * * *